US008019721B2

(12) United States Patent
Young et al.

(10) Patent No.: US 8,019,721 B2
(45) Date of Patent: Sep. 13, 2011

(54) METHOD AND SYSTEM FOR ENHANCED DATA TRANSFER

(75) Inventors: Morris J. Young, Indianapolis, IN (US); Janette Elaine Allen, Indianapolis, IN (US); Christopher Richard Baker, Fishers, IN (US); David Bradley Markisohn, Indianapolis, IN (US); Jason A. Hyden, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 636 days.

(21) Appl. No.: 11/999,911

(22) Filed: Dec. 7, 2007

(65) Prior Publication Data

US 2009/0150416 A1    Jun. 11, 2009

(51) Int. Cl.
 *G06F 7/00* (2006.01)
 *G06F 17/00* (2006.01)
(52) U.S. Cl. .................... 707/617; 707/621; 707/624
(58) Field of Classification Search .................... 707/200
 See application file for complete search history.

(56) References Cited

U.S. PATENT DOCUMENTS

| | | |
|---|---|---|
| 4,731,726 A | 3/1988 | Allen, III |
| 5,251,126 A | 10/1993 | Kahn et al. |
| 5,338,157 A | 8/1994 | Blomquist |
| 5,376,070 A | 12/1994 | Purvis et al. |
| 5,658,250 A | 8/1997 | Blomquist et al. |
| 5,665,065 A | 9/1997 | Colman et al. |
| 5,795,327 A | 8/1998 | Wilson et al. |
| 5,954,641 A | 9/1999 | Kehr et al. |
| 6,024,699 A | 2/2000 | Surwit et al. |
| 6,068,615 A | 5/2000 | Brown et al. |
| 6,102,855 A | 8/2000 | Kehr et al. |
| 6,110,148 A | 8/2000 | Brown et al. |
| 6,113,578 A | 9/2000 | Brown |
| 6,241,704 B1 | 6/2001 | Peterson et al. |
| 6,314,405 B1 | 11/2001 | Richardson |
| 6,322,502 B1 | 11/2001 | Schoenberg et al. |
| 6,368,272 B1 | 4/2002 | Porumbescu |

(Continued)

FOREIGN PATENT DOCUMENTS

EP    0 699 046    9/1996

(Continued)

OTHER PUBLICATIONS

Cabri et al.; "*Agent-based Plug-and-Play Integration of Role-Enabled Medical Devices*", IEEE Computer Society, Aug. 2007, p. 111-121.

(Continued)

*Primary Examiner* — Jay A Morrison
(74) *Attorney, Agent, or Firm* — Baker & Daniels LLP

(57) ABSTRACT

A system and method for enhanced data transfer are disclosed, the method being applicable to a system comprising a computing device configured to transfer data from a portable device. In one embodiment, the computing device stores a fingerprint of the newest record downloaded from a portable device and stops downloading records from the device when a downloaded record matches the fingerprint. In another embodiment, the computing device stores a fingerprint of the newest record downloaded from a portable device and fully processes records that are downloaded from the device after a downloaded record matches the fingerprint. The system may include a portable device configured to adapt its operation responsive to a system fingerprint provided by the computing device. The portable device may be a medical device. The system may be a healthcare data management system.

30 Claims, 7 Drawing Sheets

U.S. PATENT DOCUMENTS

| | | | |
|---|---|---|---|
| 6,427,088 B1 | 7/2002 | Bowman, IV et al. | |
| 6,470,329 B1 | 10/2002 | Livschitz | |
| 6,544,212 B2 | 4/2003 | Galley et al. | |
| 6,551,276 B1 | 4/2003 | Mann et al. | |
| 6,558,320 B1 | 5/2003 | Causey, III et al. | |
| 6,562,001 B2 | 5/2003 | Lebel et al. | |
| 6,564,105 B2 | 5/2003 | Starkweather et al. | |
| 6,571,128 B2 | 5/2003 | Lebel et al. | |
| 6,577,899 B2 | 6/2003 | Lebel et al. | |
| 6,585,644 B2 | 7/2003 | Lebel et al. | |
| 6,605,038 B1 | 8/2003 | Teller et al. | |
| 6,635,014 B2 | 10/2003 | Starkweather et al. | |
| 6,648,821 B2 | 11/2003 | Lebel et al. | |
| 6,659,948 B2 | 12/2003 | Lebel et al. | |
| 6,668,196 B1 | 12/2003 | Villegas et al. | |
| 6,671,702 B2* | 12/2003 | Kruglikov et al. | 707/201 |
| 6,687,546 B2 | 2/2004 | Lebel et al. | |
| 6,694,191 B2 | 2/2004 | Starkweather et al. | |
| 6,714,724 B1 | 3/2004 | Cook | |
| 6,733,446 B2 | 5/2004 | Lebel et al. | |
| 6,740,075 B2 | 5/2004 | Lebel et al. | |
| 6,752,787 B1 | 6/2004 | Causey, III et al. | |
| 6,758,810 B2 | 7/2004 | Lebel et al. | |
| 6,781,522 B2 | 8/2004 | Sleva et al. | |
| 6,804,656 B1 | 10/2004 | Rosenfeld et al. | |
| 6,809,653 B1 | 10/2004 | Mann et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,852,104 B2 | 2/2005 | Blomquist | |
| 6,873,268 B2 | 3/2005 | Lebel et al. | |
| 6,958,705 B2 | 10/2005 | Lebel et al. | |
| 7,020,508 B2 | 3/2006 | Stivoric et al. | |
| 7,024,236 B2 | 4/2006 | Ford et al. | |
| 7,029,455 B2 | 4/2006 | Flaherty | |
| 7,039,703 B1 | 5/2006 | Clancy et al. | |
| 7,041,468 B2 | 5/2006 | Drucker et al. | |
| 7,063,665 B2 | 6/2006 | Hasegawa et al. | |
| 7,072,356 B1 | 7/2006 | Clancy et al. | |
| 7,082,334 B2 | 7/2006 | Boute et al. | |
| 7,120,488 B2 | 10/2006 | Nova et al. | |
| 7,165,062 B2 | 1/2007 | O'Rourke | |
| 7,171,613 B1* | 1/2007 | Alexander et al. | 715/205 |
| 7,179,226 B2 | 2/2007 | Crothall et al. | |
| 7,181,350 B2 | 2/2007 | Oberding et al. | |
| 7,436,322 B2* | 10/2008 | Crank | 340/945 |
| 2002/0016568 A1 | 2/2002 | Lebel et al. | |
| 2002/0029776 A1 | 3/2002 | Blomquist | |
| 2002/0040208 A1 | 4/2002 | Flaherty et al. | |
| 2002/0143290 A1 | 10/2002 | Bui et al. | |
| 2002/0193679 A1 | 12/2002 | Malave et al. | |
| 2003/0011646 A1 | 1/2003 | Levine et al. | |
| 2003/0060765 A1 | 3/2003 | Campbell et al. | |
| 2003/0065308 A1 | 4/2003 | Lebel et al. | |
| 2003/0065536 A1 | 4/2003 | Hansen et al. | |
| 2003/0130771 A1* | 7/2003 | Crank | 701/4 |
| 2003/0163088 A1 | 8/2003 | Blomquist | |
| 2003/0163789 A1 | 8/2003 | Blomquist | |
| 2003/0193409 A1* | 10/2003 | Crank | 340/970 |
| 2003/0195904 A1* | 10/2003 | Chestnut et al. | 707/204 |
| 2004/0073464 A1 | 4/2004 | Huang | |
| 2004/0119742 A1 | 6/2004 | Silbey et al. | |
| 2004/0172284 A1 | 9/2004 | Sullivan et al. | |
| 2004/0235446 A1 | 11/2004 | Flaherty et al. | |
| 2004/0254434 A1 | 12/2004 | Goodnow et al. | |
| 2004/0260233 A1 | 12/2004 | Garibotto et al. | |
| 2005/0004947 A1 | 1/2005 | Emlet et al. | |
| 2005/0022274 A1 | 1/2005 | Campbell et al. | |
| 2005/0137653 A1 | 6/2005 | Friedman et al. | |
| 2005/0192844 A1 | 9/2005 | Esler et al. | |
| 2006/0167367 A1 | 7/2006 | Stanczak et al. | |
| 2006/0245530 A1* | 11/2006 | Pradhan et al. | 375/364 |
| 2006/0248398 A1 | 11/2006 | Neel et al. | |
| 2006/0279431 A1 | 12/2006 | Bakarania et al. | |
| 2007/0033074 A1 | 2/2007 | Nitzan et al. | |
| 2007/0048691 A1 | 3/2007 | Brown | |
| 2007/0112882 A1* | 5/2007 | Tysowski et al. | 707/201 |
| 2007/0179352 A1 | 8/2007 | Randlov et al. | |
| 2007/0185869 A1* | 8/2007 | Kirnak | 707/6 |
| 2007/0219432 A1 | 9/2007 | Thompson | |
| 2007/0248055 A1* | 10/2007 | Jain et al. | 370/331 |
| 2007/0276197 A1 | 11/2007 | Harmon | |
| 2008/0027679 A1* | 1/2008 | Shklarski | 702/182 |
| 2008/0266054 A1* | 10/2008 | Crank | 340/5.52 |

FOREIGN PATENT DOCUMENTS

| | | |
|---|---|---|
| EP | 0 970 655 | 1/2000 |
| EP | 0 649 316 B1 | 12/2000 |
| EP | 1 194 864 A2 | 4/2002 |
| EP | 1 502 614 | 2/2005 |
| EP | 1 722 310 | 4/2005 |
| WO | WO9728736 | 2/1997 |
| WO | WO9935856 | 12/1998 |
| WO | WO0018449 | 2/2000 |
| WO | WO0072181 | 11/2000 |
| WO | WO02078512 | 10/2002 |
| WO | WO02000111 | 11/2002 |
| WO | WO03015838 | 2/2003 |
| WO | WO2004090661 | 10/2004 |
| WO | WO2005011249 | 2/2005 |
| WO | WO2005037095 | 4/2005 |
| WO | WO2005096206 | 10/2005 |
| WO | WO2005114534 | 12/2005 |
| WO | WO2005114535 | 12/2005 |
| WO | WO2006050485 | 2/2006 |
| WO | WO2006108858 | 10/2006 |
| WO | WO2006118763 | 11/2006 |
| WO | WO2007/036015 | 4/2007 |
| WO | WO2007051139 | 5/2007 |
| WO | WO2007093482 | 8/2007 |
| WO | WO2008147567 | 12/2008 |

OTHER PUBLICATIONS

"The HAVi Specification—Specification of the Home Audio/Video Interoperability (HAVi) Architecture," Nov. 19, 1998, pp. 1-409, Version 1.0 beta.

Hotchkiss et al.; "MD-Adapt A Proposed Architecture for Open-Source Medical Device Interoperability", 2007, IEEE Computer Society, Aug. 2007, pp. 167-169.

"CoPilot Health Management System Version 3.1," User's Guide, Mar. 2007, 230 pp., ART 10641 Rev. D, Abbott Diabetes Care, Inc.

"MediSense® Precision Link® Diabetes Data Management Software," User's Guide, May 2006, 58 pp., 116-412 Rev. AC, Abbott Diabetes Care, Inc.

Albisser, Michael A.; "A Graphical User Interface for Diabetes Management Than Integrates Glucose Prediction and Decision Support," Diabetes Technology & Therapeutics, 2005, pp. 264-273, vol. 7, No. 2.

Janssen et al., "Acensia® Winglucofacts® Professional Intelligent Diabetes Management Software Is an Effective Tool for the Management of Diabetes," Bayer HealthCare Clinical Summary Report, Jul. 2005, 10 pp.

Joshy et al.; "Diabetes Information Systems: A Rapidly Emerging Support for Diabetes Surveillance and Care," Diabetes Technology & Therapeutics, 2006, pp. 587-597, vol. 8, No. 5.

"OneTouch Diabetes Management Software," User Manual, 2006, 173 pp., v. 2.3.1, Lifescan, Inc.

"Getting Started, CareLink Personal Therapy Management Software for Diabetes," Brochure, 2007, 20 pp., Medtronic Minimed, Inc.

"Accu-Chek® Carnit Pro Diabetes Management Software," User's Manual, 2005, 220 pp., v.2.1 and Addendum v. 2.4, Roche Diagnostics Corp.

"Accu-Chek® Compass Diabetes Care Software," User's Guide, 2005, 74 pp., Roche Diagnostics Corp.

"Accu-Chek® Diabetes Assistant," accessed with notional data and printed from www.diabetesassistant.com on Jan. 16, 2007, 20 pp., Roche Diagnostics Corp.

Partial International Search Report on Patentability for PCT/EP2008/009858 issued by the European Patent Office (2 pages).

* cited by examiner

METHOD AND SYSTEM FOR ENHANCED DATA TRANSFER

FIELD OF THE INVENTION

The invention relates to a method and system for enhanced data transfer between two or more devices.

BACKGROUND OF THE INVENTION

Many fields of medical treatment and healthcare require monitoring of certain physiological parameters. Technological advancements in medicine led to the increased use of medical devices, e.g., meters and infusion pumps, to collect medical data, and of healthcare data management systems. Healthcare data management methods and systems traditionally developed for use in healthcare facilities and health management organizations are increasingly used by patients, care givers, and others. U.S. Pat. No. 7,103,578 and U.S. Published Application No. 2004/0172284 disclose two such methods and systems. Some healthcare data management systems are able to transfer data between them.

A common feature of healthcare management systems is the ability to convey information. Information can include raw data, graphical representations of data such as statistical display objects, explanations and textual interpretations, inferential information and so on. Communication and understanding can be improved by using interactive graphs to convey information. In one particular embodiment, the development of graphical user interfaces (GUI) facilitates user interaction with data processing and other software applications. In a typical embodiment, a GUI can display a number of display objects that are individually manipulable by a user utilizing a user input device. For example, the user can utilize a computer keyboard, mouse, touch screen, touch pad, roller ball or voice commands and the like to select a particular display object and to further initiate an action corresponding to the selected display object.

Medical devices may include a data stack where patient data is recorded in anticipation of downloading to a healthcare data management system. Common methods of storing data utilize LIFO and FIFO sequential orders to store data in stacks or files. Generally, the medical device stack is downloaded in its entirety and the data is then managed by the healthcare data management system. Some medical devices retain large amounts of data and have slow transfer rates. Data transfers using those devices require an amount of time which users may consider excessive and which may conflict with their lifestyle.

SUMMARY OF THE INVENTION

A system and method for enhanced data transfer is provided. The system comprises a computing device and data management software. The computing device is configured to access a portable device containing data. In accordance with one aspect of the invention, the portable device is a medical device. The method may be implemented in the system.

In accordance with an aspect of the present invention, an enhanced data transfer method is provided. In accordance with the method, a program stores a last record fingerprint corresponding to the newest record downloaded from the portable device and stored. Upon initiation of a download event, the program receives records from the portable device in sequential LIFO order and compares each record to the last record fingerprint to find a match. Once a match is found, the program stops downloading records. Alternatively, a user may opt to download previously downloaded records.

In accordance with another aspect of the present invention, an enhanced data transfer method is provided. In accordance with the method, a program stores a last record fingerprint corresponding to the newest record downloaded from the portable device and stored. Upon initiation of a download event, the program receives records from the portable device in sequential FIFO order. The program compares each downloaded record to the last record fingerprint. Until it finds a match, the program skips further processing steps on each downloaded record. When it finds a match, the program skips further processing steps on the matched record and begins full processing of all subsequent downloaded records.

In accordance with a further aspect of the present invention, a data management system for enhanced data transfer is provided. The data management system comprises a computing device, a portable device, and data management software. The portable device is configured to receive a system fingerprint from the data management software and to adapt its operation based on a relationship between the system fingerprint and the portable device records. The system fingerprint may comprise without limitation a system identifier, a hierarchical level, and a type of data management system.

In accordance with another aspect of the present invention, an enhanced data transfer method is provided. In accordance with the method, a portable device configured to adapt its operation responsive to a system fingerprint prevents deletion of records not yet downloaded to the data management software corresponding to the system fingerprint.

In accordance with another aspect of the present invention, an enhanced data transfer method is provided. In accordance with the method, a portable device configured to adapt its operation responsive to a system fingerprint selectively downloads records to data management software based on the type of data management software.

DESCRIPTION OF THE DRAWINGS

The foregoing aspects of this invention will become more readily appreciated as the same become better understood by reference to the following detailed description when taken in conjunction with the accompanying drawings.

Figure 1:
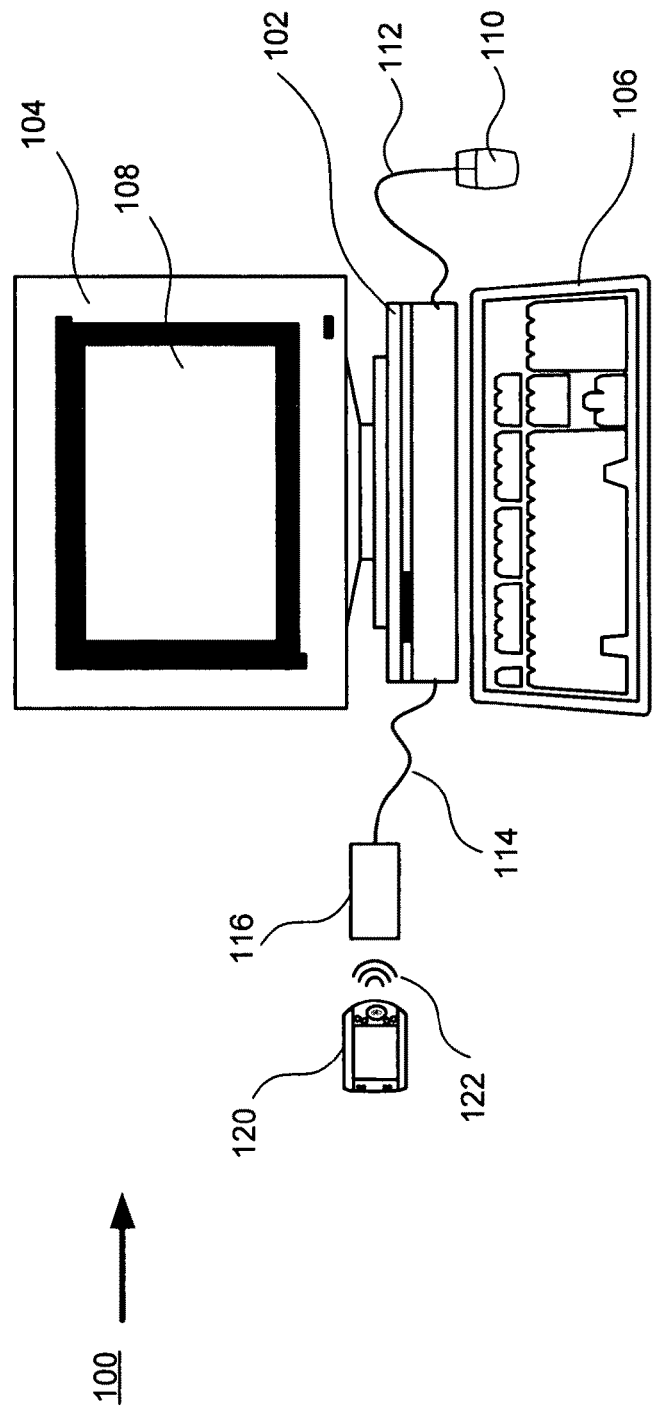
FIG. 1 is a conceptual diagram of a system according to the invention comprising a computing device having a modulated signal transceiver configured to access a portable device.

Corresponding reference characters indicate corresponding parts throughout the several views. Although the drawings represent embodiments of various features and components according to the present invention, the drawings are not necessarily to scale and certain features may be exaggerated in order to better illustrate and explain the present invention. The exemplification set out herein illustrates embodiments of the invention, and such exemplifications are not to be construed as limiting the scope of the invention in any manner.

DETAILED DESCRIPTION OF EMBODIMENTS OF THE INVENTION

Concepts described below may be further explained in one of more of the co-filed patent applications entitled HELP UTILITY FUNCTIONALITY AND ARCHITECTURE Ser. No. 11/999,906, METHOD AND SYSTEM FOR GRAPHICALLY INDICATING MULTIPLE DATA VALUES Ser. No. 11/999,853, SYSTEM AND METHOD FOR DATABASE INTEGRITY CHECKING Ser. No. 11/999,856, METHOD AND SYSTEM FOR DATA SOURCE AND MODIFICATION TRACKING Ser. No. 11/999,888, PATIENT-CENTRIC HEALTHCARE INFORMATION MAINTENANCE Ser. No. 11/999,874, EXPORT FILE FORMAT WITH MANIFEST FOR ENHANCED DATA TRANSFER Ser. No. 11/999,867, GRAPHIC ZOOM FUNCTIONALITY FOR A CUSTOM REPORT Ser. No. 11/999,932, METHOD AND SYSTEM FOR SELECTIVE MERGING OF PATIENT DATA Ser. No. 11/999,859, METHOD AND SYSTEM FOR PERSONAL MEDICAL DATA DATABASE MERGING Ser. No. 11/999,772, METHOD AND SYSTEM FOR WIRELESS DEVICE COMMUNICATION Ser. No. 11/999,879, METHOD AND SYSTEM FOR SETTING TIME BLOCKS Ser. No. 11/999,871, COMMON EXTENSIBLE DATA EXCHANGE FORMAT Ser. No. 11/999,871, METHOD OF CLONING SERVER INSTALLATION TO A NETWORK CLIENT Ser. No. 11/999,876, METHOD AND SYSTEM FOR QUERYING A DATABASE Ser. No. 11/999,912, METHOD AND SYSTEM FOR EVENT BASED DATA COMPARISON Ser. No. 11/999,921, DYNAMIC COMMUNICATION STACK Ser. No. 11/999,934, SYSTEM AND METHOD FOR REPORTING MEDICAL INFORMATION Ser. No. 11/999,878, METHOD AND SYSTEM FOR MERGING EXTENSIBLE DATA INTO A DATABASE USING GLOBALLY UNIQUE IDENTIFIERS Ser. No. 11/999,947, METHOD AND SYSTEM FOR ACTIVATING FEATURES AND FUNCTIONS OF A CONSOLIDATED SOFTWARE APPLICATION Ser. No. 11/999,880, METHOD AND SYSTEM FOR CONFIGURING A CONSOLIDATED SOFTWARE APPLICATION Ser. No. 11/999,894, METHOD AND SYSTEM FOR DATA SELECTION AND DISPLAY Ser. No. 11/999,896, METHOD AND SYSTEM FOR ASSOCIATING DATABASE CONTENT FOR SECURITY ENHANCEMENT Ser. No. 11/999,951, METHOD AND SYSTEM FOR CREATING REPORTS Ser. No. 11/999,851, METHOD AND SYSTEM FOR CREATING USER-DEFINED OUTPUTS Ser. No. 11/999,905, DATA DRIVEN COMMUNICATION PROTOCOL GRAMMAR Ser. No. 11/999,770, HEALTHCARE MANAGEMENT SYSTEM HAVING IMPROVED PRINTING OF DISPLAY SCREEN INFORMATION Ser. No. 11/999,855, METHOD AND SYSTEM FOR MULTI-DEVICE COMMUNICATION Ser. No. 11/999,866, and DEVICE AND METHOD FOR ASSESSING BLOOD GLUCOSE CONTROL Ser. No. 12/040,458, the entire disclosures of which are hereby expressly incorporated herein by reference. It should be understood that the concepts described below may relate to diabetes management software systems for tracking and analyzing health data, such as, for example, the ACCU-CHEK® 360° product provided by Roche Diagnostics. However, the concepts described herein may also have applicability to apparatuses, methods, systems, and software in fields that are unrelated to healthcare. Furthermore, it should be understood that references in this patent application to devices, meters, monitors, pumps, or related terms are intended to encompass any currently existing or later developed apparatus that includes some or all of the features attributed to the referred to apparatus, including but not limited to the ACCU-CHEK® Active, ACCU-CHEK® Aviva, ACCU-CHEK® Compact, ACCU-CHEK® Compact Plus, ACCU-CHEK® Integra, ACCU-CHEK® Go, ACCU-CHEK® Performa, ACCU-CHEK® Spirit, ACCU-CHEK® D-Tron Plus, and ACCU-CHEK® Voicemate Plus, all provided by Roche Diagnostics or divisions thereof.

For the purposes of promoting an understanding of the principles of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrated devices and described methods and further applications of the principles of the invention which would normally occur to one skilled in the art to which the invention relates.

The present invention relates to a method and system for enhanced data transfer. The system comprises a computer and data management software including applications and databases. An application, computer program, or program, is here, and generally, conceived to be a sequence of computer instructions representing steps of methods for achieving desired results. The instructions are processed by a computer and require physical manipulations of physical quantities. Usually, though not necessarily, these quantities take the form of electrical or magnetic signals capable of being stored, transferred, combined, compared, and otherwise manipulated. Programs may use data structures for both inputting information and producing the desired result. Data structures impart a physical organization on the data stored in computer memory and greatly facilitate data management. Databases include data structures and data.

The actual physical implementation of a database on a general purpose computer may take several forms, from complete individual records storing the substantive information with several key indexes for locating a particular record, to a plurality of tables interrelated by relational operations, to a matrix of cross-linked data records, to various combinations and hybrids of these general types. In particular physical devices, a database may be structured and arranged to accommodate the restrictions of the physical device but, when transferred to a general purpose computer, be able to be stored in a variety of formats. Thus, while certain types of information may be described as being stored in a "database" from a conceptual standpoint, generally such information may be electronically stored in a variety of structures with a variety of encoding techniques.

Although the following description details operations in terms of a graphic user interface using display objects, the present invention may be practiced with text based interfaces, or even with voice or visually activated interfaces.

The invention is described herein with reference to healthcare data management software, and more particularly, with reference to diabetes management software, although the invention may be applied, generally, to data management systems in fields unrelated to healthcare data management.

Before delving into the various embodiments of the system and method according to the invention, general healthcare data management system concepts will be described. A healthcare data management system receives medical data from a plurality of sources, including portable devices, and displays the data to facilitate diagnosis and treatment of patients. Data from portable devices is downloaded into the computing device before it may be managed by the system.

Turning now to the figures, FIG. 1 depicts an exemplary embodiment of a system 100 according to the invention for managing data. A particular embodiment of system 100 is the ACCU-CHEK® 360° diabetes management system distributed by Roche Diagnostics Corporation. The ACCU-CHEK® 360° receives diabetes related data from a plurality of sources, allows users to modify data, and displays data in a plurality of formats and devices. To improve communication and understanding, the ACCU-CHEK® 360° allows users to choose when and how to display information. Users can choose from a plurality of graph formats, and can also choose how to graph data. Users can combine graphs, tables, and comments on the same screen display and can view the screen display on a computer screen or can print it. Methods for customizing the presentation of data on an output device are disclosed in the above-identified co-filed patent applications.

The ACCU-CHEK® 360° software may be installed in a variety of configurations, e.g., personal and professional. The configurations determine whether some options are available to users. The ACCU-CHEK® 360° databases and software programs may be installed in a computing device comprising a personal computer or may be installed on a server. The system may download data from medical devices and may merge data from other databases. For example, a user who had been using another system may choose to upgrade to an ACCU-CHEK® 360° system. The ability to merge data allows the user to use the old data. Methods for merging data are disclosed in the above-identified co-filed patent applications. The ACCU-CHEK® 360° system may also receive medical data from multiple patients. The ACCU-CHEK® 360° software may be installed to operate in one of many languages. In the professional installation, access to a plurality of patient result databases allows the ACCU-CHEK® 360° to display information comparing a particular patient's data to statistical data corresponding groups of patients.

System 100 comprises computing device 102, shown here in the form of a computer having display device 104, in this case a computer video screen or monitor having screen 108, and keyboard 106. While described and depicted herein with specific reference to a computer, the present invention may be utilized in conjunction with any computing device capable of operating healthcare data management software including without limitation a blood glucose meter, an infusion pump, or an integrated device including a glucose measurement engine or an infusion pump. Computing device 102 has mouse 110 connected to it by cable 112. While mouse 110 and keyboard 106 are shown, system 100 may comprise any input device. System 100 includes software (not shown) configured to receive data from input devices. Components of a computing device 102 also include, but are not limited to, a processing unit and system memory.

Computing device 102 may include a variety of computer-readable media. Computer-readable media can be any available media that can be accessed by computing device 102 and includes both volatile and non-volatile media, and removable and non-removable media. By way of example, and not limitation, computer-readable media may comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules and other data and which can be accessed by computing device 102. Computer-readable media may be accessed directly or through a network or the Internet.

Computing device 102 may operate in a network environment using logical connections to one or more remote computers. The remote computer may be a personal computer, a server, a network PC, and typically includes many or all of the elements described above relative to computing device 102. The logical connections include a local area network (LAN) and a wide area network (WAN), but also include other networks. Such network environments are commonplace in office, enterprise-wide computer networks, Intranets, and the Internet. In such computer networks, typically one or more computers operate as a "server," a computer with large storage media such as hard disk drives and communication hardware to operate peripheral devices such as printers or modems. Other computers, termed "clients" or "workstations," provide a user interface so that users of computer networks can access the network resources, such as shared data files, common peripheral devices, and inter-workstation communication. The computers have at least one processor for executing machine instructions, and memory for storing instructions and other information. Many combinations of processing circuitry and information storing equipment are possible.

System 100 comprises one or more software programs. System 100 may comprise software configured to download data, to merge data from other origin databases, and to enable users to manually add and modify data. System 100 may also comprise a database for storing, retrieving, organizing, and, generally, for managing data. Data may include general data and patient data. In healthcare data management, the term "patient" refers to a person whose medical information is stored in system 100. As used herein, patient data refers to data that can identify a patient including administrative data such as name, address, phone number, and medical data such as physiological parameter values including without limitation blood glucose values, A1c values, Albumin values, Albumin excretion values, body mass index values, blood pressure values, carbohydrate values, cholesterol values (total, HDL, LDL, ratio) creatinine values, fructosamine values, HbA1 values, height values, insulin dose values, insulin rate values, total daily insulin values, ketone values, microalbumin values, proteinuria values, heart rate values, temperature values, triglyceride values, and weight values. Patient data may be provided by the patient, a healthcare professional, a medical device, a caregiver, or anyone having relevant data pertaining to a patient. In one embodiment, the databases are relational databases and the database server is the MICROSOFT SQL Server Express 2005. Computer 100 may include other applications required for operation of the SQL Server.

System 100 is configured to provide medical data to, and receive data from, medical device 120. In FIG. 1, computing device 102 includes communication media 116, in this case a modulated signal transceiver, accessible to the processor and software by means of cable 114, and configured to transmit and receive modulated signal 122 to establish logical communication with medical device 120. In another exemplary embodiment, computing device 102 and medical device 120 may include ports configured to establish a physical connection. The communication media is typically embodied by computer-readable instructions, data structures, program modules or other data in a modulated data signal such as a carrier wave or other transport mechanism and includes any information delivery media. The term "modulated data signal" means a signal that has one or more of its characteristics set or changed in such a manner to encode information in the signal. By way of example, and not limitation, communication media includes wired media such as a wired network or direct wired connection, and wireless media such as acoustic, RF, infrared and other wireless media. Combinations of any of the above are included within the scope of computer-readable media.

Medical devices are devices capable of recording medical data and transferring data to software. While the enhanced data transfer method may be performed with any portable device capable of recording data, the invention is described herein with reference to medical devices, and more particularly, with reference to diabetes management devices, e.g., meters and pumps. Medical devices may include monitors which record values of measurements relating to a patient's physiological condition and information such as the time and date when the measurement was recorded. Medical devices may also be devices configured to provide medications to patients such as, for example, insulin pumps. These devices, generally, record dosage amounts as well as the time and date when the medication was provided. Optionally, medical devices may have their own input devices and display devices. A medical device may also comprise a computing device integrated or coupled with a device for recording medical data including without limitation a computer, personal digital assistants (PDAs), phones, and BLACKBERRYs. Furthermore, system 100 may be integrated with medical device 120 thereby eliminating the necessity of generating and transmitting a modulated signal.

Medical device 120 is, generally, assigned to a patient and associated with that patient in system 100. Thus, when medical data from medical device 120 is transferred to system 100, the medical data from medical device 120 automatically populates database records relating to that patient. A user may associate medical device 120 to system 100 in various ways. In one embodiment, medical device 120 sends an unique device identifier code to the healthcare data management software. The software receives the device identifier code and associates the device with the user presently logged in and using the healthcare data management software. In another embodiment, the healthcare data management software prompts the user for confirmation before making the association. In another embodiment, the software prompts the user to select a patient and then associates the selected patient with the device.

Alternatively, medical device 120 is not associated with a patient in system 100. As disclosed below with reference to an express downloading embodiment, a download utility may receive medical device 120 data without transferring the data to a results database.

System 100 may be used by the patient, a healthcare professional, a caregiver, or anyone having relevant data pertaining to a patient. System 100 may be located in a patient's home, a healthcare facility, or any other convenient place. In an alternative embodiment, two systems may be connected and medical data may be transferred between them. For example, a first system may be located in a place accessible to the patient or a caregiver, and a second system may be located in a healthcare facility. In this embodiment, the first and second systems are configured to transfer medical data between them by any means known in the art such as, for example, via the Internet, cellular communications, or the physical transfer of a memory device such as a diskette, USB key, or compact disc. The first system, or patient system, may be configured to receive medical data from a medical device and the second system may be configured to also receive medical data from a medical device or, alternatively, to use medical data transferred from, passed-through, or accessible from, the first system. The second system, or HCP system, may be configured to receive medical data from a plurality of patient systems and medical devices. Furthermore, the HCP system may be configured to provide comments and other data to the patient system and to remotely control the patient system. In this manner, a physician using the HCP system may interact with the patient system to improve communications with the user of the patient system.

Figure 2:
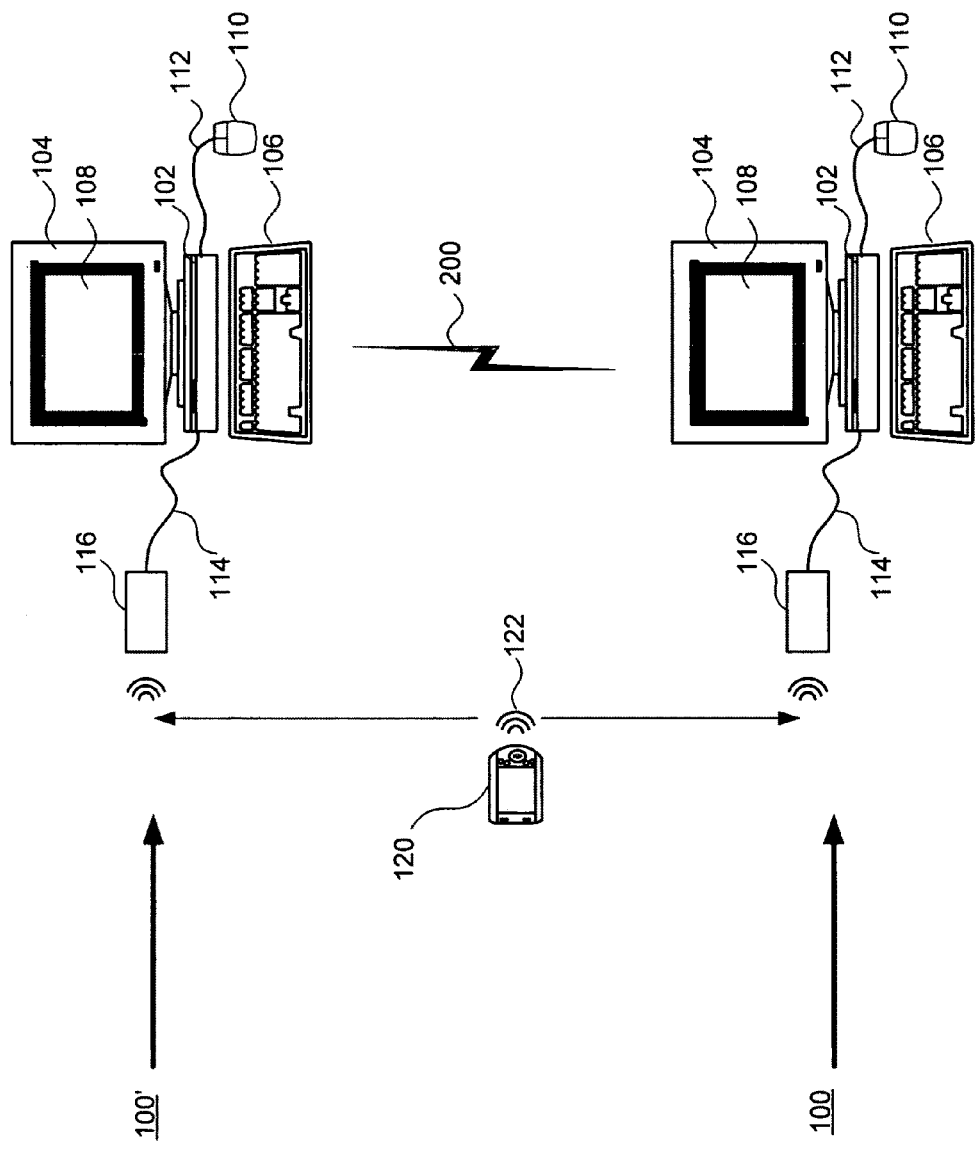
FIG. 2 is a conceptual diagram of two systems according to the invention configured to access each other and a portable device.

FIG. 2 depicts an exemplary embodiment of system 100 having access to system 100' by means of logical connection 200, and both devices having access to medical device 104. Logical connection 200 may be any means for transferring data between system 100 and system 100' including without limitation a client/server system, Internet, and removable storage media. System 100 is installed as a personal system. System 100' is installed as an HCP system. Systems 100, 100' comprise computing device 102, display device 104, input devices 106, 110, communication media 116, and healthcare data management software. In one embodiment, systems 100, 100' have access to a common results database for a patient. The results database may reside in system 100 or in system 100', or it may reside in a different system accessible to both systems 100, 100'. In another embodiment, which is disclosed more fully with reference to FIG. 7, systems 100, 100' have access to a common medical device 120.

Figure 3:
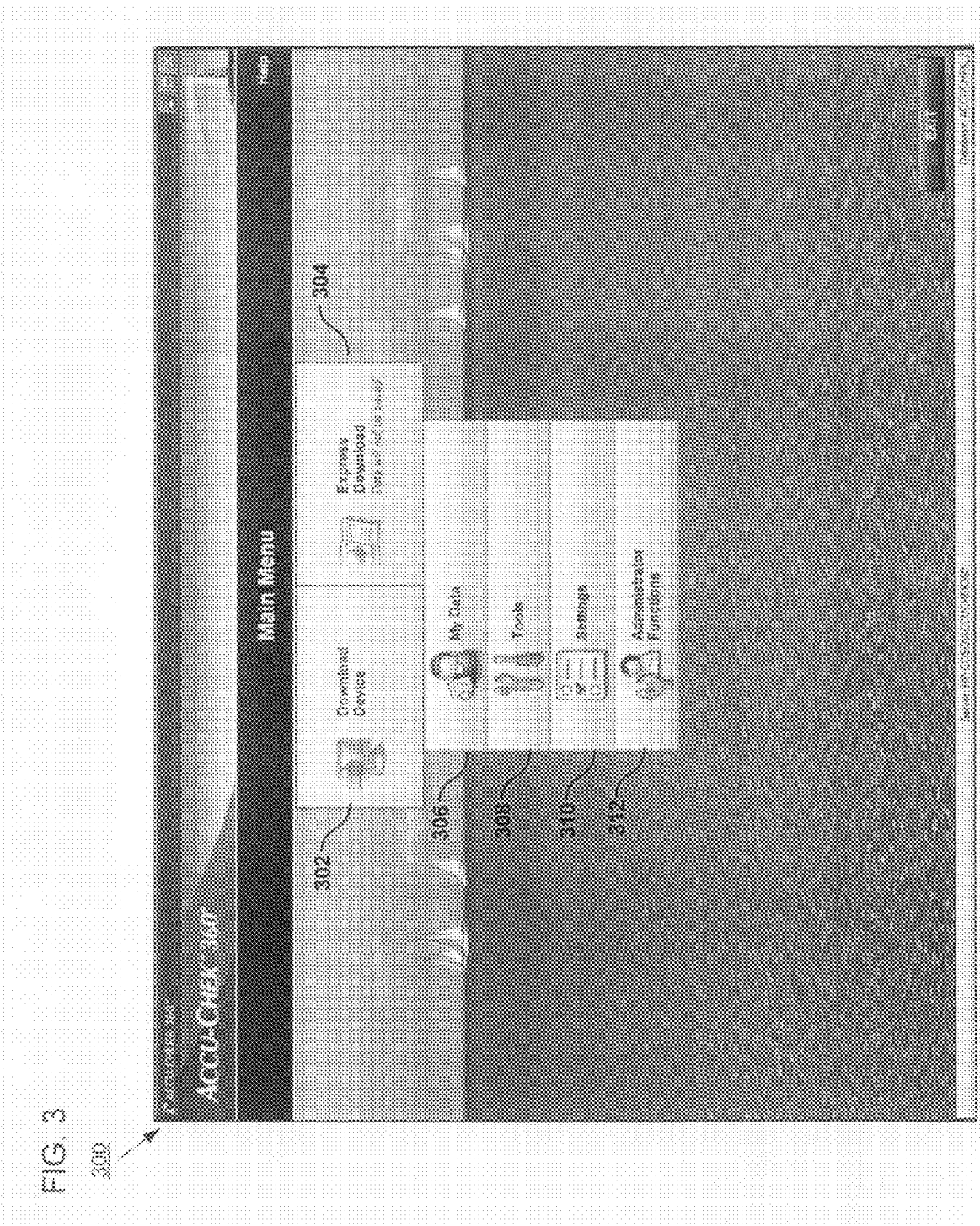
FIG. 3 is a screenshot according to the invention depicting the main menu of a personal installation of a healthcare data management software.

FIG. 3 depicts an exemplary embodiment of a user menu created in system 100 according to the invention. Screenshot 300, created by the ACCU-CHEK® 360° system in a personal installation, shows a main menu having a plurality of display objects including download device object 302, express download object 304, my data object 306, tools object 308, settings object 310, and administrator functions object 312.

Figure 4:
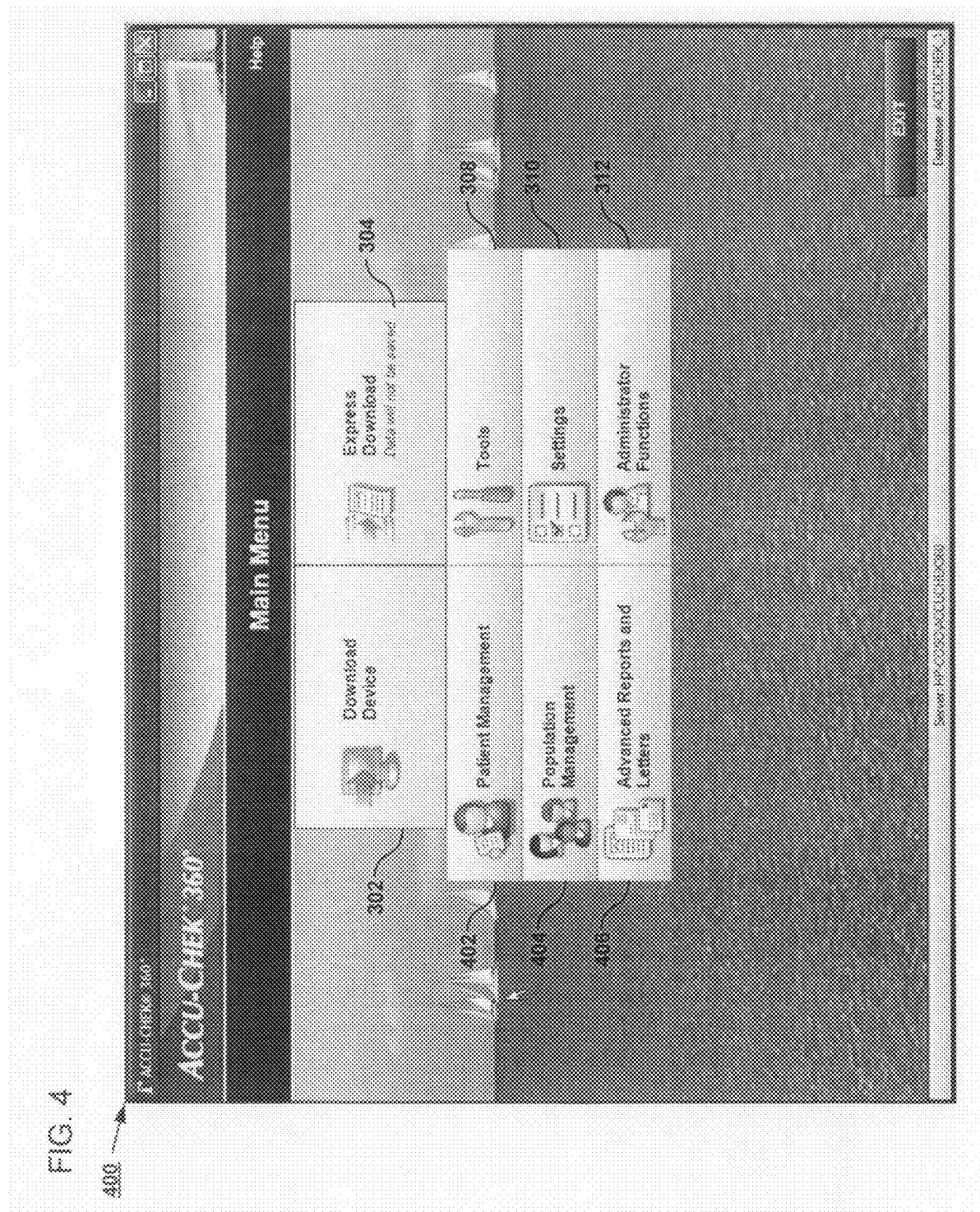
FIG. 4 is a screenshot according to the invention depicting the main menu of a professional installation of a healthcare data management software.

FIG. 4 depicts an exemplary embodiment of a user menu created in system 100' according to the invention. Screenshot 400, created by the ACCU-CHEK® 360° system in a professional installation, shows a main menu having a plurality of display objects including download device object 302, express download object 304, tools object 308, settings object 310, administrator functions object 312. Screenshot 400 also shows display objects relevant to a professional installation including patient management object 402, population management object 404, and advanced reports and letters object 406. As previously described, a professional installation provides additional features to an HCP system for managing patient populations.

Systems 100, 100' include one or more downloading utilities configured to transfer data from medical device 120. The download utility may be in the form of a computer program integrated with the healthcare data management software or may be used as an independent program, e.g., capable of independent installation and operation. In one exemplary embodiment, the download utility may be activated from the healthcare data management software after the healthcare data management software has been launched. To download data, a user activates either of download device object 302 or express download object 304. Each of objects 302, 304 are associated with a download utility. Download utilities may perform additional functions. The download utility associated with download device object 302 receives medical data from medical device 120, and performs the additional function of storing the data in a results database. The download utility associated with express download object 304 receives medical data from medical device 120, and performs the additional function of printing the data without requiring the user to access additional menu options. Methods for downloading data from a portable device are disclosed in the above-identified co-filed patent applications.

In another exemplary embodiment, the download utility may be activated without launching the healthcare data management software. A user may launch the download utility or the utility may launch automatically. The user may launch the download utility by activating a display object associated with the utility. For automatic downloading, the user may place medical device 120 such that it may be accessed by communication media 116. The automatic downloading utility may be configured to periodically send out access requests. Upon discovering a response to the request from medical device 120, the download utility may download data from medical device 120. A method for automatic detection of a portable device is disclosed in the above-identified co-filed patent applications.

Data may be stored in various formats depending on how medical device 120 is configured. As used herein, a datapoint means a point in time, or time stamp, when a portable device records data corresponding to a relevant activity, and a device record means all the data recorded by a portable device corresponding to a datapoint. The relevant activity may be the measurement of a physiological parameter, delivery of medication, or any other activity recorded by medical device 120. A device record may include without limitation a time stamp, datapoint value, and unit of measure. Some devices assign a sequence number to each record to signify the sequential order in which records are created, and include the sequence number in each record. The size of the sequence number is determined by the amount of data a portable device is projected to record during its life. The sequence number is particularly useful to identify records whose time stamps appear to be out of order. Time stamps may be out of order when a user resets the clock on the portable device, e.g., to adjust for a time zone change while traveling, or to adjust for daylight savings time changes. The clock reset may cause subsequent records to appear to have been created out of order.

In one embodiment of medical device 120, data is stored and retrieved in a last-in-first-out (LIFO) sequential order. Data may be stored in a stack or in a file or database. Storing and retrieving a device record from a stack may require multiple read/write instructions depending on the width of the stack and the amount of data in the record. A file may use characters to delimit data strings or may rely on a set string size to determine when device records begin and end. As used herein, a device record corresponds to a datapoint regardless of how the record is physically configured in medical device 120. For example, a record may be embodied as a single record in a table or as two records in different tables which are relationally linked. In a LIFO sequential order, the newest record is the first record which may be downloaded from the device. In other words, the newest record is the last record in and is downloaded before all other records are downloaded.

A download event is defined herein as the process of downloading data from medical device 120. The process begins when a download utility accesses medical device 120, and it ends when the utility stops downloading device records. During a download event, one or more device records are downloaded from medical device 120. Re-launching the download utility creates a new download event. In one embodiment, the user waits while the download utility receives data from medical device 120. In another embodiment, the user may continue to use the healthcare data management software while the download utility receives data from medical device 120 in the background.

Figure 5:
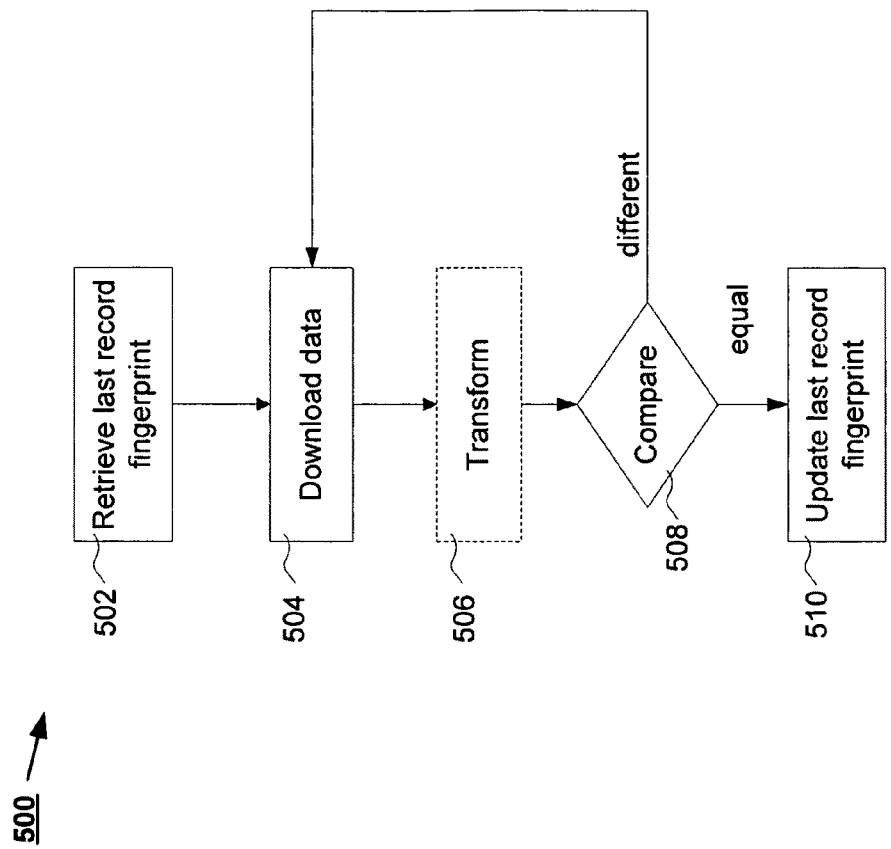
FIG. 5 is a flowchart depicting one aspect of the method according to the invention.

Referring now to FIG. 5, an enhanced data transfer method is provided. Flowchart 500 shows an embodiment of the method according to one aspect of the invention. The method may be performed by a download utility to enhance data transfers from a device that stores records in a LIFO sequential order. The method begins at Step 502 when the download utility retrieves a last record fingerprint from the healthcare data management database. Before Step 502 may be performed, the download utility must access medical device 120 and must associate medical device 120 with a patient in any manner previously described. The last record fingerprint is a data string corresponding the last device record retrieved from medical device 120 during a previous completed download event. Upon installation, the last record fingerprint corresponds to a data string signifying that no prior download event occurred. At the end of each download event, in Step 520 the download utility updates the last record fingerprint.

Generally, a fingerprint may be any data string which may be used to store information corresponding to a record. A last record fingerprint is a fingerprint corresponding to the last record retrieved during a previous download event. A fingerprint may also correspond to a database record. Fingerprints may comprise untransformed data and transformed data, e.g., coded or encrypted. In one embodiment, the last record fingerprint comprises the device record in the form downloaded from medical device 120. In another embodiment, the last record fingerprint is the encrypted value of the last device record downloaded from medical device 120. In yet another embodiment, the last record fingerprint is the hash value of the last device record downloaded from medical device 120. Cryptographic functions, including a hash function, are transformations that take an input string and return a value corresponding to the string. The value is a concise representation of the longer string from which the value was computed. The value is a sort of "digital fingerprint" of its source. A hash value is a cryptographic function that takes a long string and returns a fixed length string. A hash value is also called a digest or checksum of the stream of data that represents the contents. SHA-1, MD5, and RIPEMD-160 are commonly used hashing algorithms. Cryptographic functions may encrypt usable information into a form that is unusable by anyone except an authorized user. An authorized user may decrypt encrypted messages using the cryptographic key used to encrypt them.

Referring to Step 504 of FIG. 5, once the download utility has the last record fingerprint, it downloads a device record from medical device 120. If the last record fingerprint was stored as untransformed data, the utility proceeds to Step 508. Otherwise, the utility proceeds to Step 506 where it transforms either of the downloaded device record or the last record fingerprint to the same format. If the utility transforms the last record fingerprint to untransformed data format, the utility may temporarily store the untransformed last record fingerprint to expedite additional comparisons to additional downloaded device records. The transformation may be performed by the download utility. Alternatively, the download utility may rely upon another program to perform the transformation.

Referring to Step 508 of FIG. 5, the downloaded device record and the last record fingerprint, or their corresponding transformations, are compared to find a match. If the two items match, the downloading utility stops downloading data from medical device 120 and proceeds to update the last record fingerprint. If the two items do not match, the download utility returns to Step 504 to download another device record. A match occurs when the device record equals the untransformed last record signature. By untransformed it is meant a data string in the form of the last record before the last record is transformed to obtain its signature. Alternatively, a match occurs when a device record signature equals the last record signature. The data transfer process is enhanced by preventing downloading of previously downloaded device records. The download/transform/compare sequence repeats until a downloaded device record matches a last record fingerprint, or the respective transformation.

In one embodiment of the enhanced method according to the invention, a bypass is provided. A bypass allows the user to choose whether to prevent downloading previously downloaded records. In one embodiment of the bypass, if the user chooses to bypass, the downloading utility downloads all data from medical device 120 and proceeds to update the last record fingerprint. In another embodiment, the user may choose to bypass on a record-by-record basis. In another embodiment, the user may choose to bypass on a day-by-day basis. In yet another embodiment, the user may choose to bypass records obtained during a date range or a numbered sequence range.

Referring to Step 510 of FIG. 5, having found a match the utility updates the last record fingerprint. If system 100 stores the last record fingerprint untransformed, the last device record downloaded is stored. Otherwise, the utility transforms the last downloaded device record to obtain an encryption or hash value and then stores the value in system 100 as the last record fingerprint. The download event is completed successfully upon completion of the updating step. After updating, the download utility may perform any additional functions.

In another embodiment of the method according to the invention, an enhanced data transfer method is provided applicable to devices that store and retrieve data in first-in-first-out (FIFO) sequential order. The device may store data in a stack or in a file or database. In a FIFO sequential order, the newest record is the last record successfully downloaded from the device during a prior download event. Whether in a LIFO or FIFO system, the download process may be interrupted before a match is found. In a LIFO system, the interruption may create gaps in the sequence of records stored if the new records are fully processed, e.g., stored. The download utility may recover from the failed download by not fully processing the downloaded records in computing device 102 so as to avoid storing records created more recently than the records that were not downloaded due to the interruption. In a FIFO system according to the invention, on the other hand, records are not fully processed if a match was not found so there is no risk of storing more recent records and not storing earlier records. Consequently, once a match is found, any additionally downloaded record may be fully processed without creating gaps in the sequence of stored records. If there is an interruption, the download utility may successfully complete the download event by storing the fingerprint of the last downloaded record as the last record fingerprint.

The method begins when a download utility retrieves a last record fingerprint from a healthcare data management database. The program compares each downloaded record to the last record fingerprint. Until it finds a match, the program skips further processing steps on each downloaded record. Further processing includes, without limitation, data transformations, parsing, integrity checking, and storage. When it finds a match, the program skips further processing steps on the matched record and begins full processing of all subsequent records. Optionally, the program may provide a bypass to allow a user to fully process all records, or to fully process a selected range of previously fully processed records, in addition to unprocessed records.

In accordance with a further aspect of the present invention, a system and method for downloading data from a portable device is provided. The system comprises system 100' and medical device 600.

In one aspect of the system according to the invention, medical device 600 is configured to adapt its operation according to the relationship between the device records and a system fingerprint. In one embodiment, the relationship is hierarchical based on the last device record downloaded to one or more healthcare data management systems and the hierarchy of the healthcare data management systems. The adaptation may comprise the prevention of deletion of data that has not yet been downloaded to a system high in the hierarchy. In another embodiment, the medical device may record a plurality of types of medical data and the relationship may be based on the type of medical record and the type of healthcare data management system. The adaptations may be responsive to the system fingerprint of a healthcare data management system.

Figure 6:
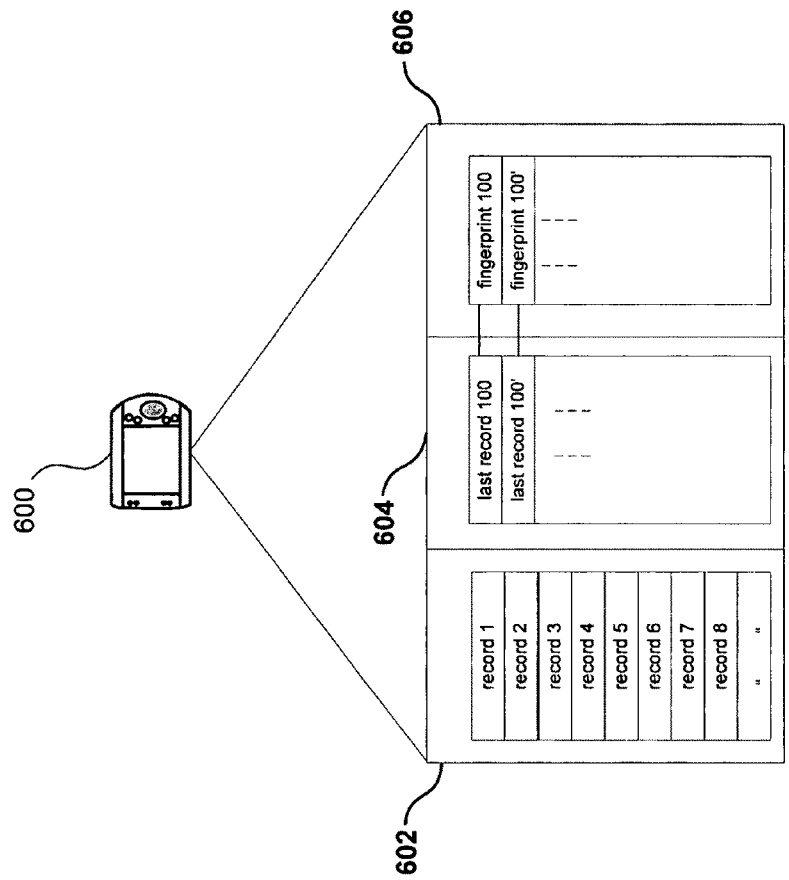
FIG. 6 is a conceptual diagram of a structural layout of computer storage media of a portable device according to the invention.

In one embodiment, the adaptation comprises the prevention of deletion of data that has not yet been downloaded to system 100'. The adaptation may be performed according to the method described below with reference to FIG. 7. Referring now to FIG. 6, medical device 600 is medical device 120 additionally configured to store one or more system fingerprints and references to the last device records downloaded to each system. Medical device 600 comprises a computer program and computer storage media having device record storage media 602, last record storage media 604, and fingerprint storage media 606. Storage media 602, 604, 606 may comprise one physical media or may be configured as separate media. System fingerprints and references to the last device record downloaded to each system may be stored in storage media 604, 606 or may be combined and stored in either of storage media 604 or 606.

Figure 7:
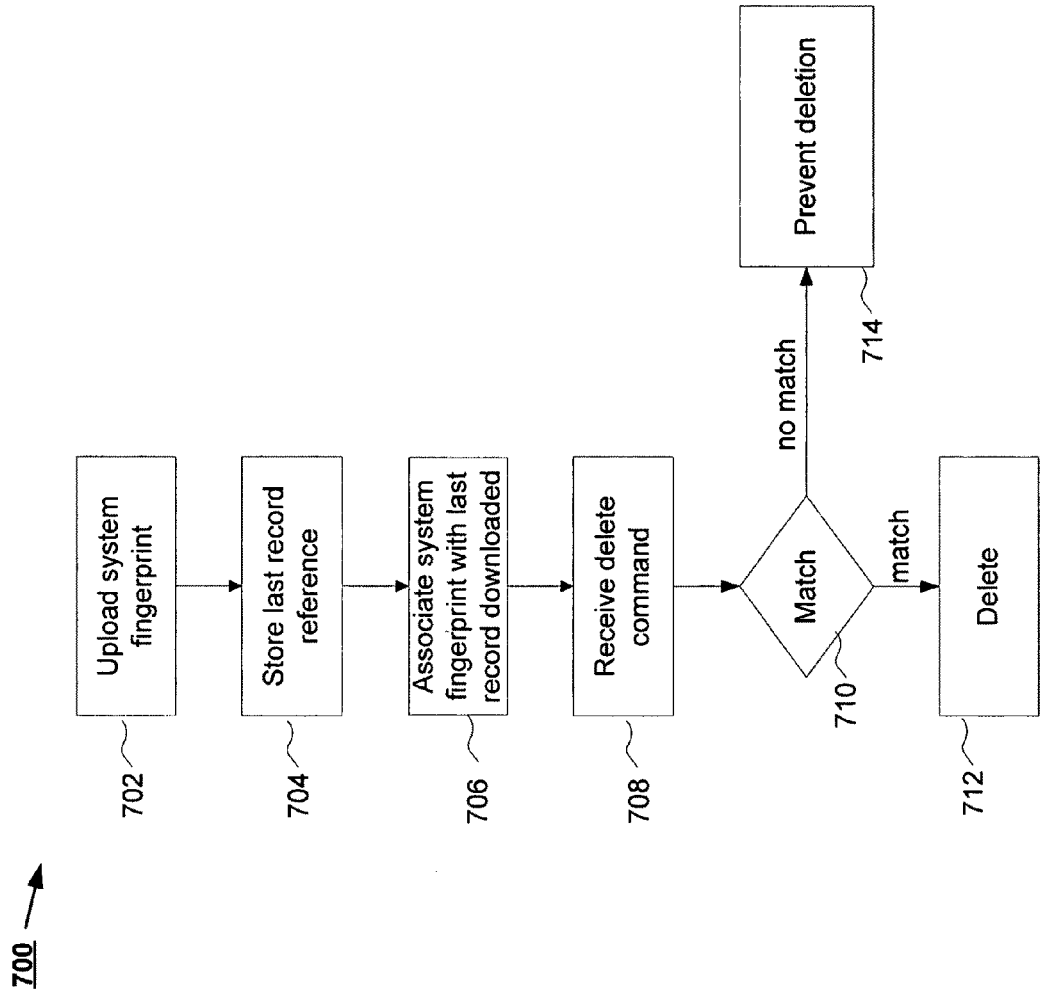
FIG. 7 is a flowchart depicting another aspect of the method according to the invention.

Referring now to FIG. 7, an enhanced data transfer method is provided. Flowchart 700 shows an embodiment of the method according to one aspect of the invention. According to the method, medical device 600 is configured to download device records to one or more systems 100, 100'. Medical device 600 may download data to system 100 installed in a patient configuration, and downloads the same data to system 100' installed in a professional configuration. Medical device 600 stores a reference to the last device record downloaded to systems 100, 100' and prevents deletion of data which has not yet been downloaded to system 100'. The method may be performed in systems 100, 100' with medical device 600 using download utilities. The method begins at Step 702 when the download utility uploads a system fingerprint from a healthcare data management database. Step 702 may occur at any time after a download event begins and before systems 100, 100' disconnect or terminate access with medical device 600. The system fingerprint is a data string corresponding to a system 100, 100' identifier. Medical device 600 stores the system fingerprint in fingerprint storage media 606. The system fingerprint may contain a code indicating the ranking of the system in a hierarchy, e.g., high, medium and low. The system may also be encoded to create other adaptive responses.

Before Step 702 may be performed, the download utility must access medical device 600 in any manner previously disclosed. The download utility downloads device records from medical device 600 until it reaches the last device record to download. The download utility may determine that the last device record to download was reached according to the method described with reference to FIG. 5, or may determine the last device record to download was reached in any other way.

Referring to Step 704 of FIG. 7, once the download utility stops downloading, medical device 600 stores a reference to the last device record downloaded in last record storage media 604. The reference may comprise the untransformed data device record or an indirect reference to the location where medical device 600 may locate the device record or a fingerprint of the device record. Then, in Step 706, medical device 600 associates the system fingerprint with the reference to the last device record downloaded to track the last device record downloaded to each system. One form of association is the combination of the system fingerprint and the reference to the last device record downloaded to each system.

Referring to Step 708 of FIG. 7, medical device 600 receives a command from a user to delete device records. The command may be to delete a range of device records or to delete all records. Upon receipt, in Step 710, medical device 600 compares the date and time of the last device record downloaded to system 100' to the date and time of the device records the user seeks to delete. In Step 712, medical device 600 prevents deletion of device records recorded later in time than the date and time of the last device record downloaded to system 100' by rejecting, or partially rejecting the user command. Partial rejection occurs when medical device 600 deletes device records created earlier in time than the last record downloaded to system 100' but does not delete more recent records. In Step 714, medical device 600 deletes device records recorded earlier in time than the date and time of the last device record downloaded to system 100'.

In another aspect of the system according to the invention, medical device 600 comprises a universal patient interface coupled to a device for performing a function including recording medical data or providing medicine. Different devices may be coupled to record different types of medical data and infuse different types of medicines. Depending on the type of device coupled to the interface, medical device 600 records different types of medical data. Medical device 600 may be configured to adapt its operation according to the relationship between the device records and different types of healthcare data management software based upon the different types of medical data recorded. According to one embodiment of the method for adapting its operation, medical device 600 may be configured to associate different system fingerprints with particular types of datapoint values corresponding to different types of devices coupled to the interface, and to only download device records having types of values corresponding to associated system fingerprints. The system fingerprint may be encoded with a code corresponding to the type of healthcare data management software to enable medical device 600 to select records. The system fingerprint may be uploaded to the medical device upon commencement of a download event.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The invention claimed is:

1. A method for enhancing data transfers comprising the steps of:

determining a data transfer method utilized by a portable device as one of a LIFO and a FIFO sequential order;
   retrieving a last record fingerprint from a computing device;
   downloading records from the portable device in the one of the FIFO and LIFO sequential order;
   transforming one of a downloaded record and the last record fingerprint to a same format as the other of the downloaded record and the last record fingerprint;
   comparing each downloaded record to only the last record fingerprint to find a match; and
   updating the last record fingerprint with a record fingerprint of a newest record downloaded,
   wherein when the LIFO sequential order data transfer method is used no additional records are downloaded after a match is found, and wherein when the FIFO sequential order data transfer method is used a step of fully processing records that are downloaded after a match is found is performed.

2. The method of claim 1 wherein the sequential order is a LIFO order, further including the steps of selecting previously downloaded records and downloading the selected records; wherein no additional previously downloaded records are downloaded.

3. The method of claim 1 wherein the sequential order is a FIFO order, further including the steps of selecting previously downloaded records and fully processing the selected records.

4. The method of claim 1 wherein the last record fingerprint is selected from the group consisting of a hash value of a record, an encrypted value of a record, and a record.

5. The method of claim 1 wherein the last record fingerprint is downloaded from the portable device.

6. The method of claim 1 wherein the last record fingerprint is obtained by transforming a record downloaded from the portable device.

7. The method of claim 1 wherein the portable device is a medical device.

8. A system for enhancing data transfers comprising:
   a computing device configured to access and download data from a portable device; and
   software configured to operate in the computing device and to:
   recognize a data transfer method utilized by the portable device as one of a LIFO and a FIFO sequential order;
   store and retrieve a last record fingerprint;
   download records from the portable device in the one of the LIFO and the FIFO sequential order;
   compare each downloaded record to only the last record fingerprint to find a match; and
   update the last record fingerprint with a record fingerprint of a newest record from the portable device downloaded to the computing device, the record fingerprint comprising untransformed data of the newest record downloaded from the portable device,
   wherein when the LIFO sequential order data transfer method is recognized no additional records are downloaded after a match is found, and wherein when the FIFO sequential order data transfer method is recognized a step of fully processing records that are downloaded after a match is found is performed.

9. The system of claim 8 wherein the software is further configured to generate a last record fingerprint.

10. The system of claim 9 wherein the last record fingerprint is selected from the group consisting of a hash value of a record, an encrypted value of a record, and a record.

11. The system of claim 8 wherein the software is healthcare data management software and the portable device is a medical device.

12. A data management system for enhancing data transfers comprising:
   a computing device;
   data management software configured to operate in the computing device and upload a system fingerprint to a portable device; and
   a portable device configured to:
      record data in records;
      receive the system fingerprint from the data management software;
      transform one of a record and a received system fingerprint to a same format as the other of the downloaded record and the system fingerprint;
      compare each record to only the system fingerprint to find a match, the system fingerprint comprising a fingerprint of a newest record downloaded to the computing device;
      transfer the records to the computing device in one of LIFO and FIFO sequential order, wherein when the LIFO sequential order is used no additional records are transferred after a match is found, and wherein when the FIFO sequential order is used records are only transferred after a match is found; and
      adapt its operations with regard to the records based on a relationship between the system fingerprint and the records.

13. The system of claim 12 where the adaptation is responsive to a code encoded in the system fingerprint.

14. The system of claim 12 where the adaptation consists of preventing deletion of records not yet downloaded to the data management software.

15. The system of claim 12 where the adaptation consists of selecting and downloading records based on the type of data management system accessible to the portable device.

16. The system of claim 12 wherein the system fingerprint further comprises a system identifier.

17. The system of claim 12 wherein the system fingerprint further comprises a type of healthcare data management system.

18. The system of claim 12 wherein the data management software is healthcare data management software.

19. The system of claim 12 wherein the data management software is diabetes management software.

20. The system of claim 12 wherein the portable device is a medical device.

21. A data management system for enhancing data transfers comprising:
   a system interface adapted to communicate with at least one computing device;
   a portable device adapted to record data in records, transfer the records in one of LIFO and FIFO sequential order to the computing device, communicate with the system interface and receive data from the system interface; and
   a data management software adapted to operate in the computing device, the computing device configured to communicate with the system interface and upload a last record fingerprint to the portable device, the last record fingerprint comprising untransformed data of a newest record downloaded from the portable device to the computing device, the portable device configured to adapt at least one of its operations with regard to receipt of data from the system interface based on a comparison of the data to the fingerprint, wherein when the LIFO sequential order data transfer method is used no additional records are transferred to the computing device after a match is found, and wherein when the FIFO sequential order data transfer method is used records are transferred to the computing device after a match is found.

22. The data management system of claim 21, wherein the last record fingerprint further comprises at least one of a type of data and a type of software.

23. The data management system of claim 21, wherein the last record fingerprint further comprises a software code.

24. The method of claim 1, further including the step of associating the portable device with a patient, wherein the last record fingerprint is associated with the patient.

25. The method of claim 1, wherein the step of transforming comprises unencrypting one of the downloaded record and the last record fingerprint.

26. The method of claim 1, further including the step of determining a type of healthcare management software utilized by the portable device, wherein the last record fingerprint is associated with the type of healthcare management software.

27. The system of claim 8, wherein the software is further configured to transform one of a downloaded record from the portable device and the last record fingerprint to a same format as the other of the downloaded record and the last record fingerprint.

28. The system of claim 27, wherein the software transforms one of the downloaded records and the last record fingerprint by unencrypting one of the downloaded record and the last record fingerprint.

29. The system of claim 8, wherein the software is further configured to associate the portable device with a patient, wherein the last record fingerprint is associated with the patient.

30. The system of claim 12 where the adaptation consists of automatically transferring data records not yet transferred upon a next communication with the data management software.

* * * * *